United States Patent

Mizuno et al.

[11] Patent Number: 5,986,088
[45] Date of Patent: Nov. 16, 1999

[54] PROCESS FOR THE PREPARATION OF AZIDE DERIVATIVES

[75] Inventors: Masanori Mizuno, Ibaraki; Takayuki Shioiri, Aichi, both of Japan

[73] Assignee: Eisai Co., Ltd., Tokyo, Japan

[21] Appl. No.: 09/032,278

[22] Filed: Feb. 27, 1998

[30] Foreign Application Priority Data

Mar. 25, 1997 [JP] Japan .................................. 9-072139
Jun. 30, 1997 [JP] Japan .................................. 9-173458
Jun. 30, 1997 [JP] Japan .................................. 9-173458

[51] Int. Cl.$^6$ .......................... C07H 1/00; C07H 5/06
[52] U.S. Cl. ................... 536/124; 536/29.1; 536/55; 552/10
[58] Field of Search ........................ 536/29.1, 55, 124; 552/10

[56] References Cited

U.S. PATENT DOCUMENTS 5,288,859  2/1994  Sabesan .................................. 536/124
5,391,772  2/1995  Thompson et al. .................... 549/292

FOREIGN PATENT DOCUMENTS

WO 95/01970  1/1995  WIPO .

OTHER PUBLICATIONS

Efficient method for the one–pot azidation of alcohols using bis(*p*–nitrophenyl) phosphorazidate XP–002070647 M. Mizuno et al, Chem. Commun., Nov. 1997, pp. 2165–2166.

*Primary Examiner*—L Eric Crane
*Attorney, Agent, or Firm*—Flynn, Thiel, Boutell & Tanis, P.C.

[57] ABSTRACT

A process for the preparation of azide derivatives useful as drugs, perfumes or intermediates of dyes by reacting an alcohol derivative with di-p-nitrophenyl phosphorazidate in the presence of 1,8-diazabicyclo[5.4.0]-7-undecene.

5 Claims, No Drawings

PROCESS FOR THE PREPARATION OF AZIDE DERIVATIVES

BACKGROUND OF INVENTION

The present invention relates to a novel and industrially advantageous process for the preparation of azide derivatives useful as drugs, perfumes or intermediates of dyes.

PRIOR ART

Up to this time, azide derivatives have been prepared by the reaction of sodium azide with halides, sulfonyl esters or phosphate esters.

Meanwhile, a process of directly reacting various alcohols with diphenyl phosphorazidate in the presence of 1,8-diazabicyclo[5.4.0]-7-undecene has been disclosed in WO-95/01970 as a process of converting alcohols into azides not through halides or the like.

However, the above process of reacting sodium azide with a halide or the like had problems that the operation had to be conducted extremely carefully due to the explosiveness of sodium azide used as the raw material, that the yields of the azides derived from secondary alcohols were low, and that the stereoselectivity of the reaction was poor.

The process disclosed in WO-95/01970 was still problematic in that the yields of azides derived from secondary alcohols were low, though it was freed from the problem of safeness of sodium azide and that of poor stereoselectivity.

As described above, an industrially satisfactory process for the preparation of azide derivatives has not been established yet, so that the development of a novel and more advantageous process has been expected.

The inventors of the present invention have intensively studied to solve the above problems. As a result of these studies, they have found that the objective azide derivatives can be prepared in high yields and at high stereoselectivity by the reaction with di-p-nitrophenyl phosphorazidate in the presence of 1,8-diazabicyclo[5.4.0]-7-undecene. The present invention has been accomplished on the basis of this finding.

SUMMARY OF INVENTION

The present invention will now be described in detail.

The present invention relates to a process for the preparation of an azide derivative (II) from an alcohol derivative (I) as represented by the following reaction formula characterized by reacting an alcohol derivative (I) with di-p-nitrophenyl phosphorazidate in the presence of 1,8-diazabicyclo[5.4.0]-7-undecene.

$$\text{ROH} \longrightarrow \text{RN}_3$$
$$\text{(I)} \qquad\quad \text{(II)}$$

wherein R is a group represented by the following general formula:

$$\left( R^2 - \underset{\underset{R^3}{|}}{\overset{\overset{R^1}{|}}{C}} - \right)$$

(wherein $R^1$ is hydrogen, lower alkyl or lower alkoxycarbonyl; $R^2$ is linear or branched alkyl, linear or branched alkenyl, linear or branched alkynyl, alkoxyalkyl, alkoxycarbonylalkyl, cyanoalkyl, optionally substituted aryl, optionally substituted aralkyl, optionally substituted heteroaryl, optionally substituted heteroarylalkyl, allyl or optionally substituted arylallyl; and $R^3$ is hydrogen, lower alkyl, lower alkenyl, lower alkoxycarbonyl or optionally substituted aralkyl), a $C_3$–$C_8$ cycloalkyl group optionally substituted with lower alkyl or lower alkoxycarbonyl, a $C_3$–$C_8$ cycloalkenyl group optionally substituted with lower alkyl or lower alkoxycarbonyl, a saccharide residue wherein part of the hydroxyl groups are protected, or a $C_3$–$C_8$ cycloalkyl group fused with an aromatic ring which is optionally substituted.

The term "lower alkyl" used in the above definition of $R^1$ in the general formula (I) or (II) refers to a $C_1$–$C_6$ alkyl group, and examples thereof include methyl, ethyl, n-propyl, i-propyl, n-butyl, i-butyl, t-butyl, n-pentyl, i-pentyl, t-pentyl, neopentyl and hexyl.

The term "lower alkoxycarbonyl" used therein refers to an alkoxycarbonyl group wherein the alkoxy moiety is a $C_1$–$C_6$ lower alkoxy group selected from among methoxy, ethoxy, n-propoxy, i-propoxy, n-butoxy, i-butoxy, t-butoxy, pentyloxy, hexyloxy and the like. Specific examples of such an alkoxycarbonyl group include methoxycarbonyl, ethoxycarbonyl, propoxycarbonyl and hexyloxycarbonyl, though the lower alkoxycarbonyl group is not limited to these groups.

The term "linear or branched alkyl" used in the definition of $R^2$ refers to an alkyl group having at most 50 carbon atoms, i.e., any of methyl to pentacontanyl groups, which may have more than one branch therein.

The term "linear or branched alkenyl" refers to an alkenyl group having at most 50 carbon atoms, i.e., vinyl or any of propenyl to pentacontaenyl groups, which may have more than one double bond or branch therein.

The term "linear or branched alkynyl" refers to an alkynyl group having at most 50 carbon atoms, i.e., ethynyl or any of propynyl to pentacontynyl groups, which may have more than one triple bond or branch therein.

The term "alkoxyalkyl" refers to a linear or branched $C_3$–$C_{50}$ alkyl group as described above which has a $C_1$–$C_6$ lower alkoxy group therein. Specific examples thereof include methoxypropyl, ethoxypropyl, methoxybutyl, ethoxybutyl, propoxypentyl and hexyloxypentacontanyl, though the alkoxyalkyl group is not limited to these groups.

The term "cyanoalkyl" refers to a linear or branched $C_1$–$C_{50}$ alkyl group having a cyano group therein. Specific examples thereof include cyanopropyl, cyanobutyl, cyanopentyl, cyanohexyl and cyanopentacontanyl, though the cyanoalkyl group is not limited to these groups.

The term "optionally substituted aryl" refers to phenyl, naphthalenyl or the like, which may be substituted with halogeno, lower alkyl, lower alkoxy, cyano, nitro, amino or the like.

The term "optionally substituted aralkyl" refers to benzyl, phenethyl or the like, which may be substituted with halogeno, lower alkyl, lower alkoxy, cyano, nitro, amino or the like.

The term "optionally substituted heteroaryl" refers to pyridyl, pyrazinyl, pyrimidyl, furanyl, pyrrolyl, thienyl, thiazolyl or the like, which may be substituted with halogeno, lower alkyl, lower alkoxy, cyano, nitro, amino or the like.

The term "optionally substituted heteroarylalkyl" refers to pyridylmethyl, pyrazinylethyl, pyrimidylpropyl, furanylbutyl, pyrrolylpentyl, thienylhexyl or the like, which may be substituted with halogeno, lower alkyl, lower alkoxy, cyano, nitro, amino or the like.

The term "allyl" refers to a group represented by the formula: $CH_2=CHCH_2-$.

The term "optionally substituted arylallyl" refers to allyl substituted with an optionally substituted aryl group as described above, for example, cinnamyl.

The term "a $C_3-C_8$ cycloalkyl group optionally substituted with lower alkyl or lower alkoxycarbonyl" refers to cyclopropyl, cyclobutyl, cyclopentyl, cyclohexyl, cycloheptyl, cyclooctyl or the like, which may be substituted with the above lower alkyl or lower alkoxycarbonyl.

The term "a $C_3-C_8$ cycloalkenyl group optionally substituted with lower alkyl or lower alkoxycarbonyl" refers specifically to cyclopropylenyl, cyclobutylenyl, cyclopentenyl, cyclohexenyl, cycloheptenyl, cyclooctenyl or the like, which may be substituted with the above lower alkyl or lower alkoxycarbonyl.

The term "a saccharide residue wherein part of the hydroxyl groups are protected" refers to a monosaccharide (such as ribose, xylose, glucose, galactose or mannose), disaccharide (such as sucrose or lactose), or other oligosaccharide wherein at least one hydroxyl group remains in a free state and the other hydroxyl groups are protected with hydroxyl-protective groups conventionally used in organic syntheses. Preferable examples of the protective group include acetyl, benzoyl, benzyl, dimethylketal residue (isopropylidene) and phenylacetal residue (benzylidene), though the protective group may be any one inert to the reaction according to the present invention.

The term "a $C_3-C_8$ cycloalkyl group fused with an aromatic ring which is optionally substituted" includes indanyl, tetrahydronaphthyl, benzocycloheptyl, benzocyclooctyl and tetrahydroanthryl, which may be each substituted with lower alkyl, lower alkoxy, halogeno, lower haloalkyl or the like on the aromatic ring.

In the present invention, 1,8-diazabicyclo[5.4.0]-7-undecene, CAS Registry No. 6674-22-2, and di-p-nitrophenyl phosphorazidate, CAS Registry No. 51250-91-0, are used, which are both known compounds and commercially available as reagents or industrial chemicals. Further, the latter can also be prepared according to the process disclosed in JP-A 48-80545, JP-A 48-67202 or the like.

DETAILED DESCRIPTION OF INVENTION

The present invention can be carried out as follows.

The order of addition of the alcohol derivative (I), 1,8-diazabicyclo[5.4.0]-7-undecene, and di-p-nitrophenyl phosphorazidate is not limited. In other words, the three compounds may be mixed at once, or two of the compounds may be premixed, followed by the addition of the remainder. In order to attain a higher yield and a higher stereoselectivity, however, it is preferable that 1,8-diazabicyclo[5.4.0]-7-undecene be added to a mixture of the alcohol derivative (I) with di-p-nitrophenyl phosphorazidate.

The amount of di-p-nitrophenyl phosphorazidate to be used is generally 1.0 to 10 equivalents, preferably 1.05 to 5 equivalents, still preferably 1.1 to 2 equivalents per equivalent of the alcohol derivative (I), though the amount is not limited.

The amount of 1,8-diazabicyclo[5.4.0]-7-undecene to be used is generally 1.0 to 10 equivalents, preferably 1.05 to 5 equivalents, still preferably 1.1 to 2 equivalents per equivalent of the alcohol derivative (I), though the amount is not limited.

The reaction may be conducted in the presence of a solvent since the use of a solvent is effective in facilitating the control of reaction temperature. The solvent usable in the present invention is not limited, but may be any one inert to the alcohol derivative (I), 1,8-diazabicyclo[5.4.0]-7-undecene and di-p-nitrophenyl phosphorazidate. Examples thereof include benzene, toluene, xylene, petroleum benzine, pentane, hexane, petroleum ether, diethyl ether, diisopropyl ether, t-butyl methyl ether, tetrahydrofuran (hereinafter abbreviated to "THF"), dioxane, dioxolane, ethylene glycol dimethyl ether, chloroform, methylene chloride, 1,2-dichloroethane, acetonitrile, ethyl acetate, butyl acetate, N,N-dimethylformamide (hereinafter abbreviated to "DMF"), 1-methyl-2-pyrrolidone, dimethyl sulfoxide (hereinafter abbreviated to "DMSO") and hexamethylphosphoramide (hereinafter abbreviated to "HMPA"), among which toluene, THF and DMF are preferable.

The amount of the solvent to be used is generally 0 to 100 ml, preferably 0.5 to 50 ml, still preferably 1 to 20 ml per gram of the alcohol derivative (I), though it is not limited.

The reaction temperature is not limited, though it may be generally up to the reflux temperature of the solvent used. Specifically, it may be selected within the range of −78 to 150° C., preferably −50 to 100° C., still preferably −30 to 50° C., in accordance with the reactivity of the starting compound.

Although the reaction time depends on the amount of the solvent used, reaction temperature and so on, the reaction is generally completed within 24 hours. After the completion of the reaction, water is added to the reaction mixture and the resulting mixture is left standing to cause phase separation; and the recovered organic phase is suitably subjected to water washing, drying and/or concentration and thereafter purified conventionally by recrystallization, various column chromatography, distillation or the like.

Examples and Comparative Examples will now be described to explain the present invention specifically, though it is needless to say that the present invention is not limited by them.

EXAMPLE

Example 1

Synthesis of 1-azidodecane

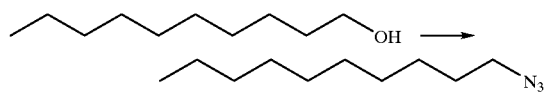

To a solution of 1.58 g (10 mmol) of 1-decanol in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 16 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.40 g of the title compound as a colorless liquid (yield: 76%).

$^1$H-NMR(400 MHz, CDCl$_3$); δ (ppm) 3.25(2H,t,J=6.8 Hz), 1.60(2H,tt,J=7.2,6.8 Hz), 1.22–1.40(14H,m), 0.88(3H, t,J=7.2 Hz). IRν max(neat); 2927, 2856, 2096, 1466, 1261 cm$^{-1}$.

Example 2

Synthesis of 2-azidodecane

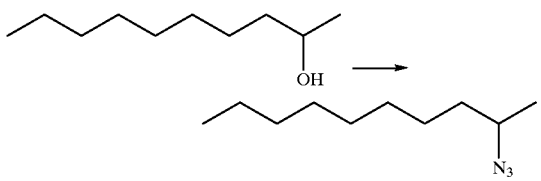

To a solution of 1.58 g (10 mmol) of 2-decanol in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 50° C. for 6 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.49 g of the title compound as a colorless liquid (yield: 81%).

$^1$H-NMR(400 MHz, CDCl$_3$); δ (ppm) 3.41(1H,tq,J=6.8, 6.4 Hz), 1.24(3H,d,J=6.4 Hz), 1.23–1.56(14H,m), 0.88(3H, t,J=7.2 Hz). IRv max(neat); 2927, 2856, 2099, 1465, 1248 cm$^{-1}$.

Example 3

Synthesis of 3-azidodecane

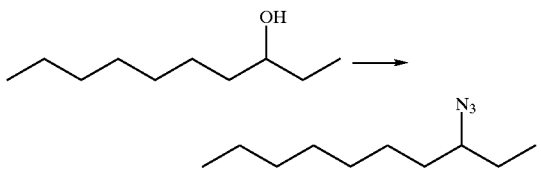

To a solution of 1.58 g (10 mmol) of 3-decanol in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 50° C. for 6 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.59 g of the title compound as a colorless liquid (yield: 87%).

$^1$H-NMR(400 MHz, CDCl$_3$); δ (ppm) 3.18(1H,tt,J=7.6, 6.4 Hz), 1.22–1.63(14H,m), 0.98(3H,t,J=7.6 Hz), 0.89(3H, t,J=6.8 Hz). IRv max(neat); 2929, 2857, 2096, 1463, 1273 cm$^{-1}$.

Example 4

Synthesis of (S)-(+)-2-azidooctane

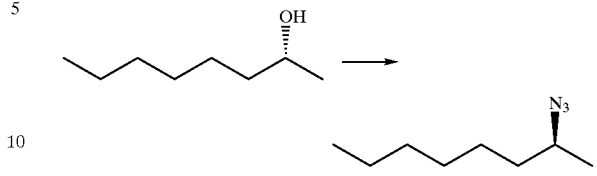

To a solution of 1.30 g (10 mmol) of (R)-(−)-2-octanol (e.e. (GC): 96.5%) in 10 ml of THF was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo [5.4.0]-7-undecene. The resulting mixture was stirred at 0° C. for 30 minutes and then at 50° C. for 6 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.40 g of the title compound as a colorless liquid (e.e. (GC): 96.3%, yield: 90%).

$^1$H-NMR(400 MHz, CDCl$_3$); δ (ppm) 3.41(1H,tq,J=6.8, 6.4 Hz), 1.24(3H,d,J=6.4 Hz), 1.22–1.56(10H,m), 0.89(3H, t,J=6.8 Hz). IRv max(neat); 2930, 2858, 2100, 1468, 1249 cm$^{-1}$. $[\alpha]^{20}_D$; +39.6° (c=1.25,CHCl$_3$).

Example 5

Synthesis of methyl (2R,3S)-2-azido-3-methylpentanoate

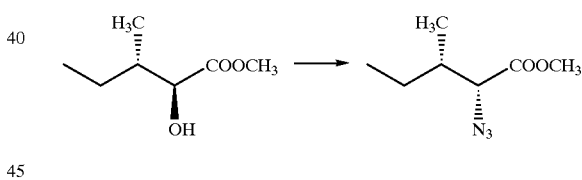

To a solution of 1.46 g (10 mmol) of methyl (2S,3S)-2-hydroxy-3-methylpentanoate (d.e. (NMR): 97.4%) in 10 ml of THF was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 50° C. for 6 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane/ethyl acetate) to give 1.21 g of the title compound as a colorless liquid (d.e. (NMR): 92.4%, yield: 71%).

$^1$H-NMR(400 MHz, CDCl$_3$); δ (ppm) 3.90(1H,d,J=4.8 Hz), 3.80(3H,s), 1.92–2.02(1H,m), 1.40–1.51(1H,m), 1.24–1.36(1H,m), 0.94(3H,t,J=7.2 Hz), 0.92(3H,d,J=6.8 Hz). IRv max(neat); 2967, 2109, 1745, 1204 cm$^{-1}$. $[\alpha]^{20}_D$; +54.9° (c=1.40,CHCl$_3$).

Example 6

Synthesis of methyl (2S,3S)-2-azido-3-methylpentanoate

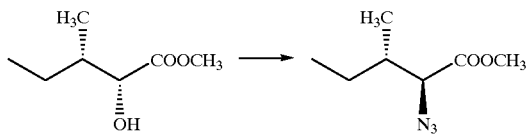

To a solution of 731 mg (5.0 mmol) of methyl (2R,3S)-2-hydroxy-3-methylpentanoate (d.e. (NMR): 97.4%) in 5 ml of THF was added 2.20 g (6.0 mmol) of di-p-nitrophenyl phosphorazidate. The resulting mixture was cooled to 0° C. under stirring, followed by the dropwise addition of 900 µl (6.0 mmol) of 1,8-diazabicyclo[5.4.0]-7-undecene. The resulting mixture was stirred at 0° C. for 30 minutes and then at 50° C., for 6 hours.

The resulting reaction mixture was diluted with 30 ml of diethyl ether, washed thrice with 10 ml of water, dried over anhydrous magnesium sulfate and concentrated in vacuo. The residue was purified by silica gel column chromatography (hexane/ethyl acetate) to give 578 mg of the title compound as a colorless liquid (d.e. (NMR): 93.4%, yield: 68%).

$^1$H-NMR(400 MHz,CDCl$_3$); δ (ppm) 3.80(3H,s), 3.72 (1H,d, J=6.4 Hz), 1.91–2.01(1H,m), 1.48–1.57(1H,m), 1.21–1.32(1H,m), 0.97(3H,d,J=6.8 Hz), 0.92(3H,t,J=7.6 Hz). IRv max(neat); 2967, 2109, 1745, 1202 cm$^{-1}$. [α]$^{20}_D$; −22.6° (c=0.86,CHCl$_3$).

Example 7

Synthesis of ethyl 2-azidophenylacetate

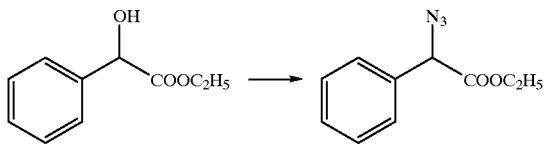

To a solution of 1.80 g (10 mmol) of ethyl mandelate in 10 ml of THF was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for one hour.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane/ethyl acetate) to give 1.99 g of the title compound as a colorless liquid (yield: 97%).

$^1$H-NMR(400 MHz, CDCl$_3$); δ (ppm) 7.37–7.44(5H,m), 4.94(1H,s), 4.17–4.31(2H,m), 1.26(3H,dd,J=7.6,6.8 Hz). IRv max(neat); 2984, 2112, 1738, 1244, 1198 cm$^{-1}$.

Example 8

Synthesis of 2,3,4,6-tetra-O-benzyl-β-D-glucopyranosyl azide

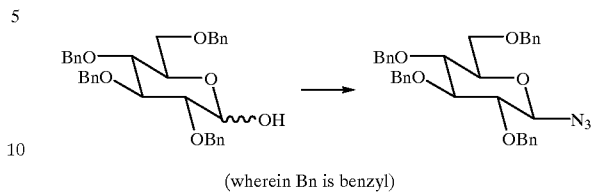

(wherein Bn is benzyl)

To a solution of 540 mg (1.0 mmol) of 2,3,4,6-tetra-O-benzyl-D-glucopyranose in 2 ml of DMF was added 438 mg (1.2 mmol) of di-p-nitrophenyl phosphorazidate. The resulting mixture was cooled to −20° C. under stirring, followed by the dropwise addition of 180 µl (1.2 mmol) of 1,8-diazabicyclo[5.4.0]-7-undecene. The resulting mixture was stirred at −20° C. for 30 minutes and then at 25° C. for 2 hours.

The resulting reaction mixture was diluted with 20 ml of ethyl acetate, washed thrice with 10 ml of water, dried over anhydrous magnesium sulfate and concentrated in vacuo. The residue was purified by silica gel column chromatography (toluene/ethyl acetate) to give 428 mg of the title compound as a colorless syrup (yield: 76%).

$^1$H-NMR(400 MHz, CDCl$_3$); δ (ppm) 7.25–7.35(18H,m), 7.12–7.16(2H,m), 4.89(1H,d,J=11.2 Hz), 4.87(1H,d,J=10.4 Hz), 4.82(1H,d,J=11.2 Hz), 4.80(1H,d,J=10.8 Hz), 4.75(1H,d,J=10.4 Hz), 4.62(1H,d,J=8.8 Hz), 4.62(1H,d,J=12.0 Hz), 4.54(1H,d,J=12.0 Hz), 4.54(1H,d,J=10.8 Hz), 3.62–3.76 (4H,m), 3.50–3.56(1H,m), 3.33–3.41(1H,m). IRv max (neat); 2115, 1092, 736, 697 cm$^{-1}$. [α]$^{20}_D$; +6.6° (c=0.91, CHCl$_3$).

Example 9

Synthesis of 2,3,4,6-tetra-O-acetyl-β-D-glucopyranosyl azide

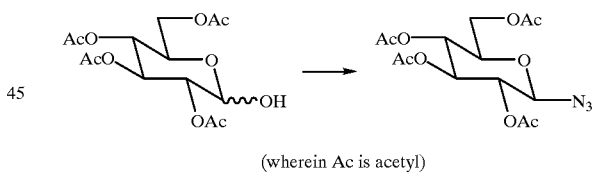

(wherein Ac is acetyl)

To a solution of 348 mg (1.0 mmol) of 2,3,4,6-tetra-O-acetyl-D-glucopyranose in 2 ml of DMF was added 438 mg (1.2 mmol) of di-p-nitrophenyl phosphorazidate. The resulting mixture was cooled to −20° C. under stirring, followed by the dropwise addition of 180 µl (1.2 mmol) of 1,8-diazabicyclo[5.4.0]-7-undecene. The resulting mixture was stirred at −20° C. for 30 minutes and then at 25° C. for 2 hours.

The resulting reaction mixture was diluted with 20 ml of ethyl acetate, washed thrice with 10 ml of water, dried over anhydrous magnesium sulfate and concentrated in vacuo. The residue was purified by silica gel column chromatography (toluene/ethyl acetate) to give 128 mg of the title compound as a colorless powder and 195 mg of the starting compound (corrected yield: 78%).

$^1$H-NMR(400 MHz, CDCl$_3$); δ (ppm) 5.22(1H,dd,J=9.6, 9.2 Hz), 5.11(1H,dd,J=10.0,9.6 Hz), 4.96(1H,dd,J=9.2,8.8

Hz), 4.65(1H, d, J=8.8 Hz), 4.28(1H,dd,J=12.4,4.8 Hz), 4.18(1H,dd,J=12.4,2.4 Hz), 3.80(1H,ddd,J=10.4,4.8,2.4 Hz), 2.11(3H,s), 2.08(3H,s), 2.04(3H, s), 2.01(3H,s). IRv max(neat); 2120, 1753, 1369, 1229, 1040 cm$^{-1}$. mp ; 125° C. $[\alpha]^{20}{}_D$; −19.1° (c=0.90,CHCl$_3$).

Example 10

Synthesis of 2,3,4,6-tetra-O-benzyl-D-galactopyranosyl azide

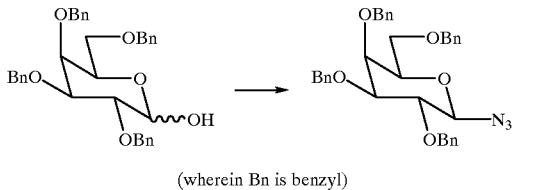

(wherein Bn is benzyl)

To a solution of 540 mg (1.0 mmol) of 2,3,4,6-tetra-O-benzyl-D-galactopyranose in 2 ml of DMF was added 438 mg (1.2 mmol) of di-p-nitrophenyl phosphorazidate. The resulting mixture was cooled to −20° C. under stirring, followed by the dropwise addition of 180 μl (1.2 mmol) of 1,8-diazabicyclo[5.4.0]-7-undecene. The resulting mixture was stirred at −20° C. for 30 minutes and then at 25° C. for 2 hours.

The resulting reaction mixture was diluted with 20 ml of ethyl acetate, washed thrice with 10 ml of water, dried over anhydrous magnesium sulfate and concentrated in vacuo. The residue was purified by silica gel column chromatography (toluene/ethyl acetate) to give 534 mg of the title compound as a colorless syrup (α/β: 1/9, yield: 94%).

$^1$H-NMR(400 MHz, CDCl$_3$); δ (ppm) 7.25–7.38(20H,m), 5.29 (1/10H,d,J=4.0 Hz), 4.59(9/10H,d,J=4.0 Hz), 4.39–4.95(8H,m), 4.11 (1/10H,dd,J=10.0,4.0 Hz), 4.02(1/10H,brdd,J=6.8,6.0 Hz), 3.92–3.96(1H,m), 3.74–3.81(1H, m), 3.50–3.64(1H,m). IRv max(neat); 2113, 1102, 735, 697 cm$^{-1}$. $[\alpha]^{20}{}_D$;+4.0° (c=1.00,CHCl$_3$).

Example 11

Synthesis of 2,3,4,6-tetra-O-benzyl-α-D-mannopyranosyl azide

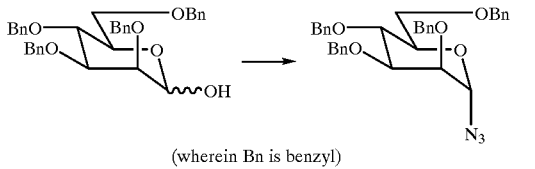

(wherein Bn is benzyl)

To a solution of 540 mg (1.0 mmol) of 2,3,4,6-tetra-O-benzyl-D-mannopyranose in 2 ml of DMF was added 438 mg (1.2 mmol) of di-p-nitrophenyl phosphorazidate. The resulting mixture was cooled to −20° C. under stirring, followed by the dropwise addition of 180 μl (1.2 mmol) of 1,8-diazabicyclo[5.4.0]-7-undecene. The resulting mixture was stirred at −20° C. for 30 minutes and then at 25° C. for 2 hours.

The resulting reaction mixutre was diluted with 20 ml of ethyl acetate, washed thrice with 10 ml of water, dried over anhydrous magnesium sulfate and concentrated in vacuo. The residue was purified by silica gel column chromatography (hexane/ethyl acetate) to give 427 mg of the title compound as a colorless syrup (yield: 75%).

$^1$H-NMR(400 MHz, CDCl$_3$); δ (ppm) 7.25–7.37(18H,m), 7.15–7.18(2H,m), 5.04(1H,d,J=2.4 Hz), 4.86(1H,d,J=10.4 Hz), 4.73(1H, d,J=12.4 Hz), 4.69(1H,d,J=12.4 Hz), 4.67(1H, d,J=12.0 Hz), 4.61 (1H,d,J=11.6 Hz), 4.58(1H,d,J=11.6 Hz), 4.54(1H,d,J=12.0 Hz), 4.51(1H,d,J=10.4 Hz), 4.02(1H,dd, J=9.6,9.6 Hz), 3.89(1H,ddd,J=9.6,4.4,2.0 Hz), 3.78–3.83 (2H,m), 3.74(1H,dd,J=11.2,2.0 Hz), 3.63(1H,dd,J=2.8,2.4 Hz). IRv max(neat); 2111, 1099, 737, 697 cm$^{-1}$. $[\alpha]^{20}{}_D$;+100.7° (c=1.28,CHCl$_3$).

Example 12

Synthesis of (E)-2-octen-1-yl azide/1-octen-3-yl azide Mixture

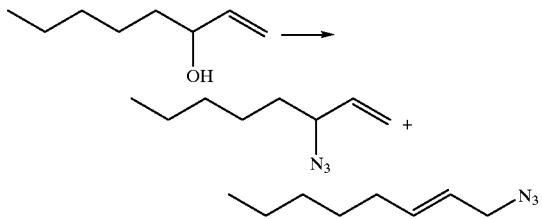

To a solution of 1.28 g (10 mmol) of (E)-2-octen-1-ol in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 2 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.26 g of the title mixture {i.e., a 1:1 (E)-2-octen-1-yl azide/1-octen-3-yl azide mixture} as a colorless liquid (yield: 82%).

$^1$H-NMR(400 MHz, CDCl$_3$); δ (ppm) 5.69–5.80(1H,m), 5.52 (1/2H,dtt,J=14.8,6.8,1.2 Hz), 5.23–5.29(1H,m), 3.80(1/2H,dt, J=7.6,7.2 Hz), 3.69(1H,d,J=6.4 Hz), 2.08(1H,dt,J=7.2,6.8 Hz), 1.24–1.58(7H,m), 0.89(3H,t,J=6.8 Hz). IRv max(neat); 2958, 2929, 2098, 1237, 971 cm$^{-1}$.

Example 13

Synthesis of 2-cyclohexen-1-yl azide

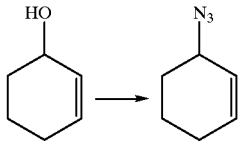

To a solution of 980 mg (10 mmol) of 2-cyclohexen-1-ol in 10 ml of THF was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 2 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 913 mg of the title compound as a colorless liquid (yield: 74%).

$^1$H-NMR(400 MHz, CDCl$_3$); δ (ppm) 5.98–6.03(1H,m), 5.68–5.73 (1H,m), 3.88(1H,brs), 1.56–2.14(6H,m). IRν max (neat); 2941, 2029, 2098, 1257, 1230, 894 cm$^{-1}$.

Example 14

Synthesis of 3-methyl-2-cyclohexen-1-yl azide/1-methyl-2-cyclohexen-1-yl azide mixture

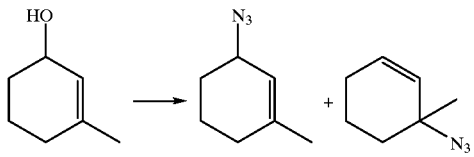

To a solution of 1.12 g (10 mmol) of 3-methyl-2-cyclohexen-1-ol in 10 ml of THF was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 2 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.06 g of the title mixture {i.e., an 8:1 3-methyl-2-cyclohexen-1-yl azide/1-methyl-2-cyclohexen-1-yl azide mixture} as a colorless liquid (yield: 77%).

$^1$H-NMR(400 MHz, CDCl$_3$); δ (ppm) 5.96(1/9H,ddd,J= 10.0, 4.0,3.6 Hz), 5.60(1/9H,ddd,J=10.0,3.2,2.4 Hz), 5.45–5.47(8/9H,m), 3.88(8/9H,brs), 1.73(24/9H,s), 1.54–2.08(6H,m), 1.30(3/9H,s). IRν max(neat); 2936, 2093, 1447, 1247, 890 cm$^{-1}$

Example 15

Synthesis of (E)-3-azido-5-methoxycarbonyl-1-cyclohexene

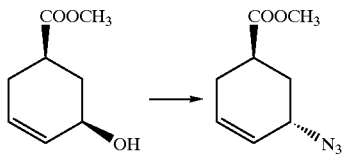

To a solution of 1.56 g (10 mmol) of (Z)-3-hydroxy-5-methoxycarbonyl-1-cyclohexene in 10 ml of THF was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for one hour.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane/ethyl acetate) to give 1.53 g of the title compound as a colorless liquid (E/Z: 97/3, yield: 84%).

$^1$H-NMR(400 MHz, CDCl$_3$); δ (ppm) 6.05(1H,dddd,J= 10.0,5.2, 2.8,1.2 Hz), 5.80(1H,m), 4.03(1H,brm), 3.71(3H, s), 2.77(1H, dddd,J=11.6,10.0,5.2,2.8 Hz), 2.40(1H,brddd, J=18.4,5.2,5.2 Hz), 2.24(1H,dddd,J=18.4,10.0,4.4,2.8 Hz), 2.14(1H,dm,J=13.6 Hz), 1.89(1H,ddd,J=13.6,11.6,4.8 Hz). IRν max(neat); 2953, 2100, 1732, 1435, 1254 cm$^{-1}$.

Example 16

Synthesis of geranyl azide/neryl azide/linalyl azide Mixture

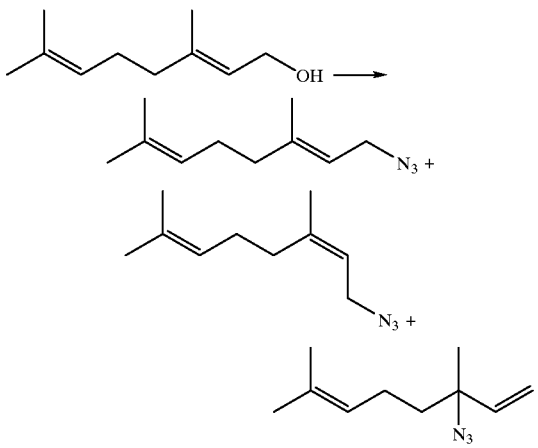

To a solution of 1.54 g (10 mmol) of geraniol in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 2 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.68 g of the title mixture {i.e., a 9:5:2 geranyl azide/neryl azide/linalyl azide mixture} as a colorless liquid (yield: 94%).

$^1$H-NMR(400 MHz, CDCl$_3$); δ (ppm) 5.78(2/16H,dd,J= 17.2, 10.4 Hz), 5.31–5.36(14/16H,m), 5.23(2/16H,dd,J= 17.2,0.8 Hz), 5.21 (2/16H,dd,J=10.4,0.8 Hz), 5.06–5.12(16/ 16H,m), 3.77(18/16H,d,J=7.6 Hz), 3.75(10/16H,J=7.2 Hz), 2.05–2.17(56/16H,m), 1.97–2.03 (4/16H,m), 1.80(15/16H, d,J=1.2 Hz), 1.71(27/16H,d,J=0.8 Hz), 1.69(48/16H,s), 1.61 (48/16H,s), 1.52–1.60(4/16H,m), 1.36 (6/16H,s). IRν max (neat); 2969, 2928, 2097, 1250 cm$^{-1}$

Example 17

Synthesis of geranyl azide/neryl azide/linalyl azide Mixture

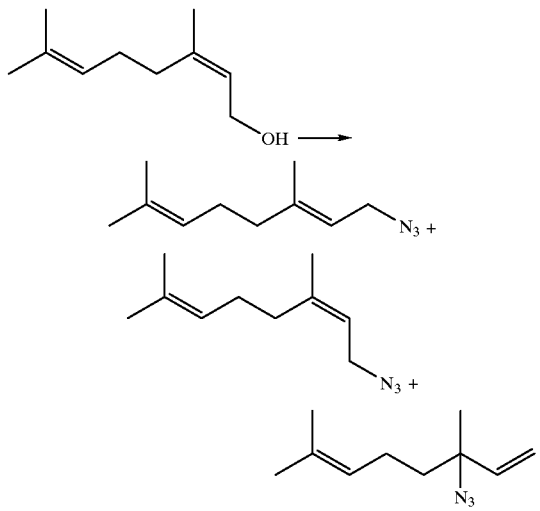

To a solution of 1.54 g (10 mmol) of nerol in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 30 minutes.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 1.70 g of the title mixture {i.e., a 3:4:1 geranyl azide/neryl azide/linalyl azide mixture} as a colorless liquid (yield: 95%).

$^1$H-NMR(400 MHz, CDCl$_3$); δ (ppm) 5.78(1/8H,dd,J=17.2, 10.4 Hz), 5.31–5.36(7/8H,m), 5.23(1/8H,dd,J=17.2, 0.8 Hz), 5.21 (1/8H,dd,J=10.4,0.8 Hz), 5.06–5.12(8/8H,m), 3.77(6/8H,d,J=7.6 Hz), 3.75(8/8H,J=7.2 Hz), 2.05–2.17(28/8H,m), 1.97–2.03 (2/8H,m), 1.80(12/8H,d,J=1.2 Hz), 1.71 (9/8H,d,J=0.8 Hz), 1.69 (24/8H,s), 1.61(24/8H,s), 1.52–1.60 (2/8H,m), 1.36(3/8H,s). IRv max(neat); 2969, 2928, 2097, 1250 cm$^{-1}$

Example 18

Synthesis of geranyl azide/neryl azide/linalyl azide Mixture

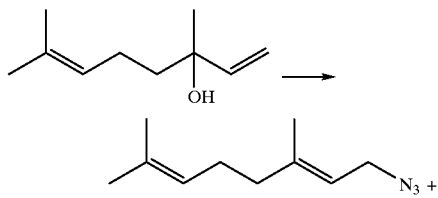

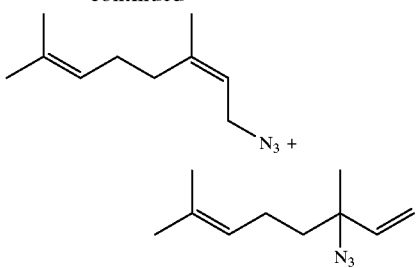

To a solution of 1.54 g (10 mmol) of linalool in 10 ml of toluene was added 4.38 g (12 mmol) of di-p-nitrophenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 2 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 537 mg of the title mixture {i.e., a 7:10:3 geranyl azide/nerylazide/linalyl azide mixture} as a colorless liquid and 936 mg of the starting compound (corrected yield: 77%).

$^1$H-NMR(400 MHz, CDCl$_3$); δ (ppm) 5.78(3/20H,dd,J=17.2, 10.4 Hz), 5.31–5.36(17/20H,m), 5.23(3/20H,dd,J=17.2,0.8 Hz), 5.21 (3/20H,dd,J=10.4,0.8 Hz), 5.06–5.12(20/20H,m), 3.77(14/20H,d,J=7.6 Hz), 3.75(20/20H,J=7.2 Hz), 2.05–2.17(68/20H,m), 1.97–2.03 (6/20H,m), 1.80(30/20H,d,J=1.2 Hz), 1.71(21/20H,d,J=0.8 Hz),1.69 (60/20H,s), 1.61 (60/20H,s), 1.52–1.60(6/20H,m), 1.36(9/20H,s). IRv max (neat); 2969, 2928, 2097, 1250 cm$^{-1}$

Example 19

Synthesis of (S)-1-phenylethyl azide

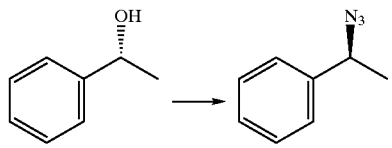

To a solution of 611 mg (5.0 mmol) of (R)-1-phenylethanol (e.e.(GC): 100%) in 5 ml of THF was added 2.20 g (6.0 mmol) of di-p-nitrophenyl phosphorazidate. The resulting mixture was cooled to 0° C. under stirring, followed by the dropwise addition of 900 μl (6.0 mmol) of 1,8-diazabicyclo[5.4.0]-7-undecene. The resulting mixture was stirred at 0° C. for 30 minutes and then at 25° C. for one hour.

The resulting reaction mixture was diluted with 30 ml of diethyl ether, washed thrice with 10 ml of water, dried over anhydrous magnesium sulfate and concentrated in vacuo. The residue was purified by silica gel column chromatography (hexane/ethyl acetate) to give 691 mg of the title compound as a colorless liquid (e.e. (GC): 100%, yield: 94%).

$^1$H-NMR(400 MHz, CDCl$_3$); δ (ppm) 7.29–7.41(5H,m), 4.61(1H, q,J=6.8 Hz), 1.53(3H,d,J=6.8 Hz). IRv max(neat); 2980, 2105, 1454, 1248, 699 cm$^{-1}$. $[\alpha]^{20}_D$; −105.0° (c=1.10, CHCl$_3$).

Example 20

Synthesis of (S)-1-azidoindan

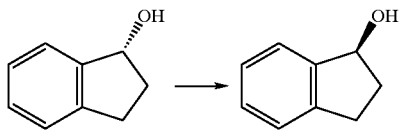

To a solution of 671 mg (5.0 mmol) of (R)-1-indanol (e.e. (GC): 100%) in 5 ml of THF was added 2.20 g (6.0 mmol) of di-p-nitrophenyl phosphorazidate. The resulting mixture was cooled to 0° C. under stirring, followed by the dropwise addition of 900 μl (6.0 mmol) of 1,8-diazabicyclo[5.4.0]-7-undecene. The resulting mixture was stirred at 0° C. for 30 minutes and then at 25° C. for 2 hours.

The resulting reaction mixture was diluted with 30 ml of diethyl ether, washed thrice with 10 ml of water, dried over anhydrous magnesium sulfate and concentrated in vacuo. The residue was purified by silica gel column chromatography (hexane) to give 654 mg of the title compound as a colorless liquid (e.e. (GC): 81.3%, yield: 82%).

$^1$H-NMR(400 MHz, CDCl$_3$); δ (ppm) 7.39(1H,dd,J=7.2, 0.4 Hz), 7.23–7.31(3H,m), 4.86(1H,dd,J=7.2,4.4 Hz), 3.07 (1H,ddd,J=16.0 8.4,6.4 Hz), 2.87(1H,ddd,J=16.0,8.4,5.2 Hz), 2.44(1H,dddd,J=13.2,8.4,7.2,6.4 Hz), 2.12(1H,dddd,J= 13.2,8.4,5.2,4.4 Hz). IRν max(neat); 2946, 2092, 1325, 1287, 755 cm$^{-1}$. [α]$^{20}$$_D$; −9.0° (c=0.99,CHCl$_3$).

Example 21

Synthesis of (S)-2-phenyl-1-(2-thiazolyl)-ethyl azide

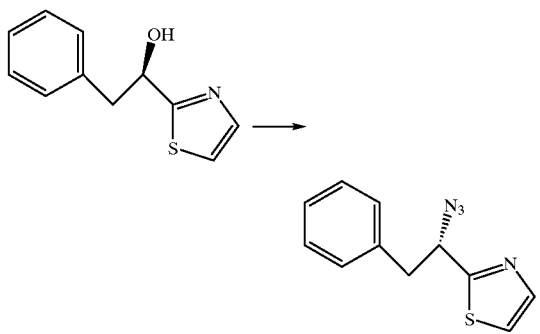

To a solution of 103 mg (0.5 mmol) of (R)-2-phenyl-1-(2-thiazolyl)ethanol (e.e. (HPLC): 95.9%) in 0.5 ml of THF was added 219 mg (0.6 mmol) of di-p-nitrophenyl phosphorazidate. The resulting mixture was cooled to 0° C. under stirring, followed by the dropwise addition of 90 μl (0.6 mmol) of 1,8-diazabicyclo[5.4.0]-7-undecene. The resulting mixture was stirred at 0° C. for 30 minutes and then at 25° C. for 3 hours.

The resulting reaction mixture was diluted with 20 ml of diethyl ether, washed thrice with 10 ml of water, dried over anhydrous magnesium sulfate and concentrated in vacuo. The residue was purified by silica gel column chromatography (hexane/ethyl acetate) to give 105 mg of the title compound as a colorless liquid (e.e. (HPLC): 95.6%, yield: 91%).

$^1$H-NMR(400 MHz, CDCl$_3$); δ (ppm) 7.81(1H,d,J=3.2 Hz), 7.22–7.33(6H,m), 5.01(1H,dd,J=8.8,4.8 Hz), 3.42(1H, dd,J=14.0,4.8 Hz), 3.17(1H,dd,J=14.0,8.8 Hz). IRν max (neat); 3029, 2105, 1497, 1308, 1247, 732, 700 cm$^{-1}$. [α]$^{20}$$_D$;−36.2° (c=1.03,CHCl$_3$).

Comparative Example 1

Synthesis of 1-azidodecane (According to the Process using diphenyl phosphorazidate)

To a solution of 1.58 g (10 mmol) of 1-decanol in 10 ml of toluene was added 2.59 ml (12 mmol) of diphenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 25° C. for 24 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 95 mg of the title compound as a colorless liquid (yield: 5%).

Comparative Example 2

Synthesis of 2-azidodecane (According to the Process using diphenyl phosphorazidate)

To a solution of 1.58 g (10 mmol) of 2-decanol in 10 ml of toluene was added 2.59 ml (12 mmol) of diphenyl phosphorazidate. The resulting mixture was cooled to 0° C. under stirring, followed by the dropwise addition of 1.8 ml (12 mmol) of 1,8-diazabicyclo[5.4.0]-7-undecene. The resulting mixture was stirred at 0° C. for 30 minutes and then at 50° C. for 6 hours.

The resulting reaction mixture was diluted with 50 ml of diethyl ether, washed thrice with 20 ml of water, dried over anhydrous magnesium sulfate and concentrated in vacuo. The residue was purified by silica gel column chromatography (hexane) to give 63 mg of the title compound as a colorless liquid (yield: 3%).

We claim:

1. A process for the preparation of azide derivatives represented by the general formula: RN$_3$, wherein R is selected from the groups consisting of a group represented by the following general formula:

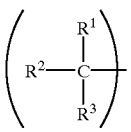

, wherein R$^1$ is selected from the group consisting of hydrogen, lower alkyl and lower alkoxycarbonyl, R$^2$ is selected from the group consisting of linear or branched alkyl, linear or branched alkenyl, linear or branched alkynyl, alkoxyalkyl, alkoxycarbonylalkyl, cyanoalkyl, optionally substituted aryl, optionally substituted aralkyl, optionally substituted heteroaryl, optionally substituted heteroarylalkyl, allyl and optionally substituted arylallyl, and R$^3$ is selected from the group consisting of hydrogen, lower alkyl, lower alkenyl, lower alkoxycarbonyl and optionally substituted aralkyl; a C$_3$–C$_8$ cycloalkyl group optionally substituted with loweralkyl or lower alkoxycarbonyl; a C$_3$–C$_8$ cycloalkenyl group optionally substituted with lower alkyl or lower alkoxycarbonyl; a saccharide residue wherein part of the hydroxyl groups are protected;

and a $C_3$–$C_8$ cycloalkyl group fused with an aromatic ring which is optionally substituted, wherein the improvement comprises reacting an alcohol derivative represented by the general formula: ROH, wherein R is as defined above, with di-p-nitrophenyl phosphorazidate in the presence of 1,8-diazabicyclo[5.4.0]-7-undecene.

2. The process for the preparation of azide derivatives according to claim 1, wherein 1,8-diazabicyclo[5.4.0]-7-undecene is added to a mixture of the alcohol derivative with di-p-nitrophenyl phosphorazidate.

3. The process for the preparation of azide derivatives according to claim 1, wherein R is selected from the groups consisting of a group represented by the following general formula:

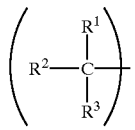

, wherein $R^1$ is selected from the group consisting of hydrogen, lower alkyl and lower alkoxycarbonyl, $R^2$ is selected from the group consisting of linear or branched $C_1$–$C_{50}$ alkyl, linear or branched $C_2$–$C_{50}$ alkenyl, linear or branched $C_2$–$C_{50}$ alkynyl, optionally substituted aryl and optionally substituted heteroaryl, and $R^3$ is selected from the group consisting of hydrogen, lower alkyl, lower alkenyl, lower alkoxycarbonyl and optionally substituted aralkyl; a $C_3$–$C_8$ cycloalkenyl group optionally substituted with lower alkyl or lower alkoxycarbonyl; a pyranosyl group wherein part of the hydroxyl groups are protected; and a $C_3$–$C_8$ cycloalkyl group fused with an aromatic ring which is optionally substituted.

4. The process for the preparation of the azide derivatives according to claim 1, wherein R is selected from the groups consisting of a group represented by the following general formula:

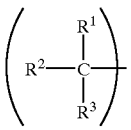

, wherein $R^1$ is selected from the group consisting of hydrogen, lower alkyl and lower alkoxycarbonyl, $R^2$ is selected from the group consisting of linear or branched $C_1$–$C_{20}$ alkyl, linear or branched $C_2$–$C_{50}$ alkenyl, aryl and heteroaryl, and $R^3$ is selected from the group consisting of hydrogen, lower alkyl, lower alkenyl, lower alkoxycarbonyl and aralkyl; a $C_3$–$C_8$ cycloalkenyl group; a pyranosyl group wherein part of the hydroxyl groups are protected with a member selected from the group consisting of acetyl, benzoyl, benzyl, a dimethylketal moiety and a phenylacetal moiety; and a $C_3$–$C_8$ cycloalkyl group fused with an aromatic ring.

5. The process for the preparation of azide derivatives according to claim 1, wherein the alcohol derivative is selected from the group consisting of 1-decanol, 2-decanol, 3-decanol, 2-octanol, a 2-hydroxy-3-methylpentanoate ester, a mandelate ester, 2,3,4,6-tetra-O-benzyl-D-glucopyranose, 2,3,4,6-tetra-O-acetyl-D-glucopyranose, 2,3,4,6-tetra-O-benzyl-D-galactopyranose, 2,3,4,6-tetra-O-benzyl-D-mannopyranose, 2-octen-1-ol, 2-cyclohexen-1-ol, methyl-2-cyclohexen-1-ol, 3-hydroxy-5-alkoxycarbonyl-1-cyclohexene, geraniol, nerol, linalool, 1-phenylethanol, 1-indanol and 2-phenyl-1-(2-thiazolyl)ethanol.

* * * * *